United States Patent [19]
Ulmer et al.

[11] Patent Number: 5,555,895
[45] Date of Patent: Sep. 17, 1996

[54] PROCESS AND DEVICE FOR EYE MOVEMENT ANALYSIS

[75] Inventors: Erik Ulmer, Marseilles; Philippe Guillemant, Carnoux, both of France

[73] Assignee: Centre National De La Recherche Scientifique, Paris, France

[21] Appl. No.: 295,815

[22] PCT Filed: Jan. 28, 1994

[86] PCT No.: PCT/FR94/00108

§ 371 Date: Sep. 21, 1994

§ 102(e) Date: Sep. 21, 1994

[87] PCT Pub. No.: WO94/16612

PCT Pub. Date: Aug. 4, 1994

[30] Foreign Application Priority Data

Jan. 29, 1993 [FR] France ................................. 93 01268

[51] Int. Cl.⁶ .................................................. A61B 3/10
[52] U.S. Cl. ........................ 128/782; 128/749; 351/210
[58] Field of Search .................................. 351/209, 210, 351/246; 128/774, 782

[56] References Cited

U.S. PATENT DOCUMENTS 4,613,219  9/1986  Vogel ........................................ 357/209
4,852,988  8/1989  Velez et al. .
5,218,387  6/1993  Ueno et al. ............................. 351/210

FOREIGN PATENT DOCUMENTS 0125808  11/1984  European Pat. Off. .
0456166  11/1991  European Pat. Off. .
2207748  2/1989  United Kingdom .

OTHER PUBLICATIONS

Medical And Biological Engineering And Computing, vol. 28, No. 4, Juillet 1990, Stevenage GB pp. 317–324.
Yamada, et al, "Development of an eye–movement analyser possesing functions for wireless transmission and autocalibration." voir p. 318, ligne 31—p. 320, ligne 19; Fig. 1,2.

*Primary Examiner*—Sam Rimell
*Attorney, Agent, or Firm*—Dvorak and Traub

[57] ABSTRACT

The present invention relates to a process and a device for analyzing the movement of the eye or eyes of a patient, i.e. of a human being or animal. A device comprising a first video camera, a second video camera, which first and second cameras are mounted on a spectacle frame and are rigidly connected together and form part of a removable module; said dirst and second cameras have points of sight of their respective scenes which are close. The technical domain of the invention is that of the manufacture of devices for measuring the movement of the eyes.

8 Claims, 4 Drawing Sheets

PROCESS AND DEVICE FOR EYE MOVEMENT ANALYSIS

BACKGROUND OF THE INVENTION

The present invention relates to a process and device for analyzing the movement of the eye or eyes of a patient, i.e. of a human being or animal.

The technical domain of the invention is that of the manufacture of devices for measuring the movement of the eyes.

The interest of the invention is, above all, medical. Its preferred application is the exploration of vertigos and disorders of balance, which are one of the principal pathologies with which doctors are faced (one patient out of twenty in general practice).

In this domain of preferred application of the invention, the eye is considered as an indicator of the activity of the vestibulum (or posterior labyrinth), which is an organ of balance located in the internal ear sensitive to the absolute position as well as to the movements of the head. This organ influences by reflex (therefore involuntarily) the tonus of all the skeletal muscles, in particular that of the eye muscles. When it is stimulated, either by movements of the head, or artificially, in particular by thermal effects in the internal ear, the vestibulum is capable of inducing automatic movements of the eyes or nystagmus, which are synchronous for the two eyes. Consequently, the observation of either one of these two eyes (if the eye muscles are normal) is an excellent reflection of the functioning of the vestibulum. However, account must be taken of a considerable constraint which results from the fact that the eye also responds to visual stimulations and that the system of vision takes priority and is more powerful than that of the vestibulum: observation of the nystagmus therefore indicates the functioning of the internal ear only if the patient is in total darkness, i.e. if his/her two eyes receive no visible light.

To test the vestibulum from the oculomotor indicator, several conditions must therefore be complied with:

- the eye movements must be able to be permanently observed and/or analyzed during all the tests of the examination.
- the examination must be able to verify the normality of the voluntary eye movements and reflexes of visual origin, during so-called "tracking tests" which consist in projecting fixed or mobile targets or visual stimuli proposed for the patient's sight in the scene.
- the natural vestibular stimuli of displacement to which the patient is subjected and for which the oculomotor response is studied (essentially the movements of his head with respect to the scene or his head with respect to his thorax) must be able to be recorded and analyzed at the same time as the movements of the control eye.
- the examination must be able to include so-called "vestibular tests" during which the total absence of light visible solely by the patient is rendered necessary.

In order better to understand the object of the present invention, account must also be taken of the fact that the constraint of tightness to visible light, although it is indispensable for the exploration of the vestibular activity, may become limitative in the case of more restrictive examinations made by other doctors, for whom the observation and analysis of the ocular movements presents a slightly different interest, when for example solely tracking tests or follow-up and analysis tests of the sight are made. In that case, a device according to the preferred application might be unsuitable if it does not provide in its embodiment that the solution made to the condition of tightness is carried out only as supplementary, secondary option, independent of the basic device.

The principal object of the present invention is therefore to provide a device and process for observation, measuring and analysis of eye movements, which makes it possible to implement during the same, preferably medical examination, the following four priorities, except the last for certain examinations, namely in order of priority, firstly, the necessity of being able to observe and/or analyze the movement of an eye at least during the whole of the examination; secondly, the necessity of being able to liberate the field of vision of an eye at least facing the scene; thirdly, the necessity of being able to observe and/or analyze, at the same time as the movements of at least one eye, all the visual and vestibular ocular stimuli, i.e. the movements of the visual targets with respect to the head, the movements of the head with respect to the scene and the movements of the head with respect to the thorax; fourthly, the necessity of being able totally to occult the two eyes from any visible light, i.e. of being able to place the patient in complete darkness during part of the examination.

Another object of the invention is to provide a device which is ergonomic, capable of being adapted to the morphology and/or sight of the patient, and of being economical, compact and light.

Patent Application EP 125 808 to WEINBLATT already discloses an eye movement measuring device which comprises a spectacle frame and which comprises, as shown in FIG. 2 of this document, a scene camera connected to optics fixed on a side piece of the spectacles by optical fibers, and which also comprises an eye observing camera connected to optics fixed on the spectacle frame, likewise via optical fibers; the video signals produced by the two cameras are combined to furnish an image corresponding to the superposition of the scene image with the image of the eye, which images are observed by the two cameras.

One object of the invention is to provide a device for measuring and analyzing the movement of the eyes comprising an eye observing camera and a camera for observing the scene in which the patient is placed, which device is improved with respect to the one described in the above document, whilst remaining compatible with the principal object. Other Patents or publications on eye movement measuring devices are also known, which comprise a scene camera in relation with an eye observing camera, in which the scene camera is placed and equipped so as to visualize, approximately or exactly, the field of vision of the observer. This latter object is not shared as far as the present invention is concerned, for which the sole function of the visualization of the scene is the observation and calculation of the relative movements of objects of the scene with respect to the patient's (observer's) head, and may consequently not correspond at all to the field of vision of the observer (as nothing prevents, in a particular configuration of the device, placing or projecting the objects of the device on the ceiling of the examination room and directing the scene camera upwardly), which has for its advantage to allow the present invention a freedom of configuration of the device in accordance with criteria which are adapted to the preferred examination and which bear on the positioning of the scene camera with respect to the ocular camera.

SUMMARY OF THE INVENTION

The objects of the invention are attained by providing an eye movement analysis device comprising a first video camera, capable of delivering a first video signal representative of an image of said eye, which device further comprises a second video camera, capable of delivering at least a second video camera representative of an image of a scene, which first camera and second camera are mounted on a spectacle frame, in which said first camera and second camera are rigidly connected together mechanically and form part of a removable module, and in which said first camera and second camera have points of sight of their respective scenes which are close.

The invention procures a eye movement measuring and analysis device comprising an eye observing camera, and a camera observing the scene in which the patient is placed, which exploits a configuration of the position of these two cameras (with respect to each other) which is both the most practical, mechanically, and optimum so that the calculations of the relative movements of the objects of the images of the eye and of the scene with respect to the two cameras are simplified, more rapid and more precise, so that the components of these movements are easier to correlate with respect to one another, and the prior adjustments and calibration necessary before effecting the measurements are facilitated.

According to a preferred embodiment, the invention provides a device for measuring and/or analyzing the movement of the eye and/or the movements of the eyes of a patient, i.e. of a human being or animal, comprising at least a first video camera, sensitive to infrared light and particularly to the light of the domain of the near infrared, and preferably sensitive to at least a part of the visible light, which first video camera is capable of delivering at least a first video signal representative of an image of said eye; said device further comprises at least a second video camera, sensitive to infrared light and particularly to the light of the domain of the near infrared, preferably sensitive to at least a part of the visible light, which second video camera is capable of delivering at least a second video signal representative of an image of a scene, such as an object at least and/or a scene and/or a picture and/or a screen on which an image may be projected, which scene is close to and/or located in the vicinity of said patient; said first camera and second cameras are mounted on a mask or spectacle frame, adapted to be worn by the patient, said first and second cameras are substantially rigidly connected mechanically together; said device comprises a module which is easily removable or interchangeable by fitting or clipping for example on said mask, said module comprises said first and second video cameras, and said first and second cameras have points of sight of their respective scenes (i.e. for example their optical focus or their image focal plane) which are close and preferably substantially merged, and have axes of their respective fields of vision corresponding to the lines or columns of their two images, which have at least one common direction.

Said first and second cameras advantageously have respective optical axes substantially parallel to each other and close, preferably substantially merged, which first and second cameras are mounted with respect to each other in a "head-to-tail" or "back-to-back" configuration, i.e. symmetrically with respect to a median plane, which is substantially perpendicular to the direction in which said patient is looking at said scene, i.e. said plane of symmetry is substantially vertical and perpendicular to the axis of sight or of observation of the patient.

Said device advantageously comprises means for digitalizing said second video signal, said device comprises means for analyzing and/or processing the digital data corresponding to said second digitalized signal and/or to said digitalized scene images obtained, which analyzing means comprise contour extraction means, preferably comprise means for identifying at least one object appearing in said scene image, and comprise means for calculating coordinates of said object.

The device advantageously comprises means for digitalizing the first video signal and means for analyzing the digitalized images of the eye obtained, which means for analyzing and/or processing the digital data corresponding to the first digitalized video signal, comprise specialized means for detecting the pupil and means for extracting contours of objects, means for identifying these objects and means for calculating the coordinates of the centre of the pupil and the other objects extracted from the image of the eye.

Said module, comprising said first and second video cameras, advantageously comprises a first monochrome matrix CCD sensor and a second monochrome matrix CCD sensor, which first and second CCD sensors are preferably identical and are located in two planes substantially parallel to each other, perpendicular to said substantially merged optical axes of said cameras, and symmetrical with respect to said plane of symmetry, which planes and/or which CCD sensors are very close to one another, for example located at a distance, measured on the optical axis common to said cameras, which is of the order of 1 to 50 mm, preferably at a distance close to or less than 10 mm.

Said device advantageously comprises means for synchronizing said first and second video signals and means for multiplexing said first and second video signals to form a first multiplexed video signal composed of two even and odd frames, of which one (even or odd) is identical to the simultaneous frame of said first video signal and of which the second (odd or even, respectively) is identical to the simultaneous frame of said second video signal.

Said device advantageously comprises means for synchronizing said first and second video signals and means for multiplexing said first and second video signals to form a second multiplexed video signal, which second multiplexed video signal is composed of two even and odd frames, which each comprise a consecutive assembly of lines which are, preferably alternately, identical to lines of said first and second video signals issuing respectively from said first and second video cameras.

The device advantageously comprises a mask or spectacle frame which may be provided by fitting or clipping two modules chosen from an assembly of modules equipping the device, which assembly of modules comprises at least two removable modules, which modules being, on the one hand, the principal module composed of a camera for observing the eye and a camera for observing the scene and, on the other hand, a module for observing and/or analyzing the eye comprising one camera, said modules both comprising means, such as diodes, for lighting the eye with infrared light.

The device advantageously comprises a mask or spectacle frame provided with light-tight means so that the fitting or clipping of two modules on said mask makes it possible to form in front of the patient's eyes a black room or a volume tight with respect to the out, de visible light, and the assembly of modules of the device advantageously comprises a particular module which comprises an obturator or shutter presenting no camera. Furthermore, withdrawal of one of these modules from this mask makes it possible advantageously to clear in front of one of the patient's eyes an opening enabling him to see the scene at a sufficient angle (+/−25°, or 50° at least in total).

One of the modules of the device advantageously comprises, for certain examinations requiring a high frequency of acquisition of the ocular movements, a camera for observation and/or analysis of the eye, and means such as diodes for lighting the eye with infrared light, and means such as photoreceptors for receiving the light intensity reflected by the eyeball.

Said scene or environment advantageously comprises at least one fixed or mobile contrasted mark or object, and said device preferably comprises means for projecting at least one light spot, of visible or infrared light, on said environment or scene, which light spot constitutes one of said fixed or mobile, contrasted marks, which projection means are preferably mechanically connected to the patient's body, preferably to his chest.

Said device advantageously comprises second means for lighting said scene and/or for projecting a mark in said scene, which lighting means are preferably mechanically connected to said removable module.

The measuring devices according to the invention procure numerous advantages.

In fact, thanks to the modular configuration of the devices rendering independent the eye observation module and the mask having for function the fixation of this module on the head, the mask may be freely chosen to be tight or non-tight with respect to the visible light, depending on the needs of the examination. Thanks to this choice rendered possible, a spectacle frame reduced to its most simple expression may be used for certain examinations, i.e. constituted for example solely by one eyepiece in which a module is fitted or clipped, which makes it possible completely to liberate the field of vision of at least one eye, thus providing a greater advantage for studying the position of the look. Furthermore, thanks to the two openings made on a tight mask and to the removable screens constituted by different modules, the device lends itself equally well to examinations in the presence of visible light for which a sufficient field of vision remains through an opening, and to examinations in which a black room, tight with respect to the outside visible light, must be provided in front of the patient's eyes.

Thanks to the principal module of the device which is of removable nature and easily held in the hand, this module may be used before being positioned on the mask worn by the patient, by simply being held by an operator's or doctor's fingertips, to indicate to the analysis system one or more particular objects of the scene to be identified, for example by orienting the module so as to place these objects one by one approximately at the centre of the image delivered by the scene camera, such initial identification being useful for memorizing the characteristics of these objects and subsequently for making it possible to quantify the relative movements of the module (and therefore the movements of the patient's head) from the identification a posteriori of the position of these same objects displaced in the image. In fact, it may be difficult to have the patient carry out this operation himself by moving his head when the module is placed on his mask, since the patient does not necessarily see the display screen on which the image delivered by the scene camera appears.

Thanks to the configuration whereby the two cameras of the principal module have points of sight of their respective scenes which are close and preferably merged, a parameter is eliminated by being cancelled or disregarded, which is a hindrance as it is non-angular of distance between the optical axes which intervenes in the transformation of the apparent angular coordinates of objects of the mark of a camera to that of another and which makes it necessary to estimate, to make the necessary angular corrections, the distances from the cameras to the objects used for calculating their movements. Thanks to said configuration, the knowledge and awkward use of these highly fluctuating-distances is rendered unnecessary, which is in particular and advantageously the case of the "head-to-tail" configuration.

Thanks to the configuration whereby the two cameras have axes of their respective fields of vision corresponding to the lines or columns of their two images, which share at least a common direction, the purely horizontal movements of the eye with the head straight (or the horizontal movements of the mask with respect to the head) may correspond to purely horizontal movements of the fixed objects of the scene, and the purely vertical movements of the eye with the head straight (or the vertical movements of the mask with respect to the head) may correspond to purely vertical movements of the fixed objects of the scene, which enables the components of these movements, calculated by electronic image processing, to be immediately available during a usual examination without calibration for analysis and correlation of the movements and which simplifies the calculations which are also rendered more rapid and easier to effect in real time on a simple micro-computer.

Thanks to the configuration whereby the two cameras are assembled inside a module or removable casing and preferably when the two cameras are mounted "head-to-tail", the dimensions of the two cameras are reduced to a minimum and the presence of the scene camera does not increase the part of the field of vision of the patient already occulted by the first eye observing camera; in the case of using an eye observing camera and a scene observing camera and/or corresponding identical CCD sensors, said cameras and said CCD sensors are easier to house in the same casing which may contain the electronic means for pre-processing the signals issuing from the CCD sensors and facilitate the connection between the module removably fixed to the spectacle frame and the signal processing device which may be incorporated in a micro-computer.

Thanks to the modular and preferably "head-to-tail" configuration making it possible to bring the two cameras inside a casing or principal module as close as possible, in which said casing or module removably fixed on the spectacle frame comprises the electronic means for controlling and synchronizing the measurements of the CCD sensors, the phenomena of electro-magnetic parasites which may interfere on the measuring signals may be avoided; finally, said casing or removable module may contain the electronics for supplying diodes for lighting the eye with infrared light and for receiving signals delivered by photoreceptors, in the case of using such photoreceptors which are integrated in said module and which make it possible to observe at least two components of movement of the eye, with a much higher pass band than the standard video pass band which is of the order of 25 Hertz.

Thanks to the configuration of said cameras and/or said CCD sensors whose optical axes are merged and which are mounted "head-to-tail", the images delivered by said cameras are more simple to correlate and the calculation of the movements of the objects of the scene, particularly with respect to the position of the eyes, is more precise; thanks to the position of the cameras whose optical axes are merged, the calibration of the device is simplified; in fact, in the case of a possible temporary withdrawal of the mask or the spectacle frame by the patient or a simple readjustment of said frame with respect to the patient's head, said readjustment provokes an indetermination on the position of the cameras with respect to the head, which may create errors in the movements calculated from the images of said cameras. Thanks to the correction of the errors on the eye movements which may be made at least in part by using as reference mark naturally contrasted zones of the face which are fixed with respect to the head, and thanks to said "head-to-tail" configuration, the errors on the movements of the objects of the scene may also be corrected at least in part, using the same mark, which may make it possible to avoid a fresh calibration due to this readjustment of the mask.

Thanks to the configuration of the preferred device used with a tight mask, for which there exist on this mask two ocular openings adapted to be obturated by two distinct removable modules, each eye may be observed and/or analyzed with a different module, therefore possibly with different processes of analysis, different sensors, different lightings, and two different analyses or tests which are impossible to make simultaneously on the same eye, may thus be made simultaneously on two eyes. For example, in the case of difficulty in positioning on a small surface of the same module, diodes, photoreceptors and lens necessary for a particularly demanding analysis (such as that of the jerks of the eye which requires a high pass band of the order of 250 Hz), a right-hand module equipped with diodes and lens and a left-hand module equipped with diodes and photoreceptors may be used. Such specialization or differentiation of the modules is furthermore necessary, taking into account the fact that it is unnecessary therefore expensive to use two scene cameras, therefore it is advantageous to observe and/or analyze the two eyes simultaneously in the dark thanks to a module equipped with one camera of ocular type, accompanying the principal module equipped with two cameras. It is also advantageous to be able to use a module reduced to its simplest function of screen or of "shutter" to make generally sufficient monocular tests, thus lightening the device.

Thanks to the configuration of the device comprising means directed on one eye or on the two eyes for analyzing the synchronous ocular movements per camera with simultaneously means for analyzing the ocular movements by sensors of light intensity reflected by the eyeball, such as photoreceptors, two complementary pass bands for analysis of these movements are available, respectively low frequency and high frequency, which may advantageously be combined by an operation of processing of the signal amounting to an addition for each horizontal or vertical axis on the one hand of the ocular displacements recorded by photoreceptors and issuing from a high pass filter (>25 Hz) and on the other hand of the ocular displacements calculated by image processing and issuing from a low pass filter (<25 Hz), so as to form a high frequency ocular response reset without calibration (or with automatic calibration) on the exact movements of the eye, which very advantageously avoids having to use image acquisition and processing frequencies higher than 25 Hz.

Furthermore, photoreceptors may advantageously also be placed on the other face of a module to pick up the light intensity issuing from the scene and to increase in accordance with the same principle the frequency of measurement of the relative movements of the head with respect to the targets or light marks.

Thanks to the means for analysis and/or processing of the digital data of the image of the digitalized scene obtained, and in particular thanks to the contour extraction means with which the device is provided, the contours of the fixed objects naturally present or artificially placed (for the needs of the examination) in the scene may be calculated, processed and recognized individually so as to follow each object in its movement to deduce therefrom at least the apparent horizontal, vertical and rotary coordinates of the movement of the head with respect to the scene.

Thanks to the same means for analysis and/or processing of the data and for extraction of contour of the image of an eye obtained, the contours of the pupil and reflections of the diodes on the cornea, as well as other objects of the ocular image, may be identified and allow in particular the calculation of the coordinates of the centre of the pupil.

Furthermore, in the embodiment where lighting means connected to the patient's chest are provided, which project a mare in the scene, the position of the corresponding mark may be determined by the same means for analysis of the image delivered by the scene camera and thus make it possible to determine by follow-up of the coordinates of the mobile mark projected, the movements of the patient's chest or body with respect to the scene.

Thanks to the invention, it is therefore possible to analyze at the same time as the ocular movements, not only the labyrinth and cervical proprioceptor stimuli which are at the origin of these ocular movements and which necessitate the measurement of the relative movements between the head and the scene and/or between the patient's head and chest, but also the visual stimuli which may be obtained by the same results of the scene image analysis furnishing the coordinates of the objects constituted by the visual mobile targets proposed for the patient's sight, which are distinct from the possibly infrared mobile targets proposed to the scene camera and not to the patient.

Thanks to the invention, by one sole analysis of the scene image, the use of very numerous sensors or stimulation devices, which, without the invention, are indispensable, such as for example the use of an armchair electronically servo-controlled with the acquisition of the movement of this armchair on which the patient is sitting, the acquisition of the movements of his head (accelerometers and/or magnetometers), or the acquisition of the movement of motors for rotating light-ray projecting mirrors, may thus be avoided.

Thanks to the multiplexing of the images of the eye and of the scene in which these images alternately share consecutive assemblies of lines of the same image (for example the eye at the top of the image and the scene at the bottom), the doctor may record on a video recorder a qualitative trace of the visual stimulis or the movements of the patient's head at the same time as his ocular movements which may allow him a demonstration or a rapid qualitative diagnosis in deferred time.

Thanks to the multiplexing of the images of the eye and of the scene for which these images alternately share the two frames of the same image, the image processing device may work on a single video signal, which simplifies the image acquisition electronics, reduces the electronic cost of the device, and makes it possible to enter the complete image of the eye and the head at the same time as the complete image of the scene, on video recorder and on micro-computer.

Thanks to infrared lighting means for the scene mechanically connected to the removable module, there may be used as fixed objects in a dark room, for calculating the head/scene movements, objects invisible for the patient such as for example naturally present forms or pellets voluntarily placed on the dark walls having the particularity of reflecting this infrared lighting more or less, while, of course, remaining invisible to the patient's view.

Thanks to the process of analysis of the scene of the device consisting in calculating the apparent movement of the scene with respect to the head by identifying the successive positions of the same object in the scene image, and thanks to the following process of calculation of this movement, when the angular dynamics are greater than the angle of the lens of the scene camera, consisting in relaying the identification of a reference object leaving this field of vision by the identification of another reference object appearing in this field of vision and therefore better placed, the device is capable of simulating the slow phases and the jerks of a correct movement of nystagmus that the patient's eyes may or should produce, by possibly advantageously using the result of the calculation of the position of his look to help in identifying a new object of the image of the scene to be tracked for calculating its apparent movement.

In a preferred embodiment of a device according to the invention, the eye movements are measured in the following manner:

in a window of the image centred on the mean position of the pupil and delivered by said first camera or eye observing camera, the contour of a shape corresponding to the pupil is isolated;

if necessary, the contour of the pupil is rectified so as to render it substantially circular;

the geometric centre of gravity of the contour, which is the position of the centre of the pupil, i.e. its two coordinates in a plane, is calculated;

an angular portion of a ring located around the image of said pupil (comprising striae, in known manner) is compared or correlated with a previously recorded image of said angular ring, and an angle of rotation of said angular ring corresponding to an angle of rotation in said plane of said eye, is deduced.

In a preferred mode of carrying out the process for analyzing the movement of the patient's head, the following operations are carried out:

a window or a part of the scene image furnished by the second camera is used, said window being able, in a particular embodiment, to move in said image, the contours of different objects detected in said window are extracted, and the centres of gravity of the objects and/or of the corresponding contours are calculated, the contours thus detected which do not have a number of points included in an interval centred around the previously recorded number of points of a predetermined and sought after object, are eliminated, for each remaining contour, predetermined reduced contour shape functions are calculated, said reduced contour shape functions thus determined are compared with previously recorded contour shape functions corresponding to the sought-after object, the position in said window of said object thus identified is calculated and, in a particular embodiment, said window is recentred around said object.

Advantageously, it is possible to display simultaneously, in "virtually real" time, i.e. at a frequency of the order of 25 hertz, an image of a window or part of the image of the eye and an image of a window or part of the scene image, curves of variation as a function of time of the position of the centre of the pupil determined as indicated hereinabove, and possibly a curve of the rotation of said pupil as a function of time, and curves of the position of said identified object corresponding to the apparent movements of the head.

Advantageously, it is possible to display in "virtually real" time, for the visual control of the calculations, a cross indicating the calculated centre of the pupil on the image of the eye, which cross may possibly be inclined to reflect the result of the calculation of the rotation of the pupil.

The numerous advantages procured by the invention will be more readily understood on reading the following description with reference to the accompanying drawings, which illustrate in non-limiting manner particular embodiments of devices according to the invention.

DESCRIPTION OF THE PREFERRED EMBODIMENT

Referring now to the drawings, the device according to the invention comprises a removable module 16 comprising a casing (reference 28 of FIG. 3) which receives a video camera 3 for observing the eye 2 of a patient, and a video camera 5 for observing the scene 7 observed by the patient whose look is directed substantially in the direction represented by arrow 29.

Figure 2:
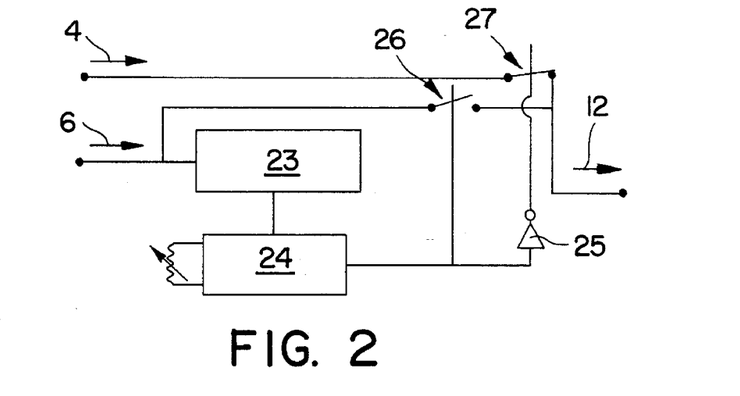
FIG. 2 schematically illustrates means for multiplexing the video signals delivered by the eye and scene observing cameras of a device according to the invention.
Figure 4:
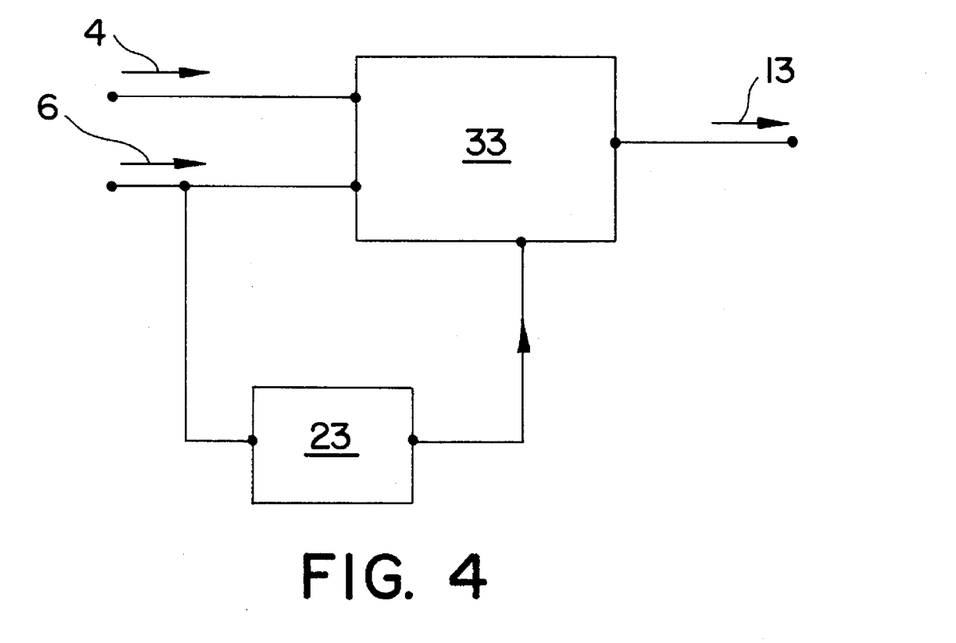
FIG. 4 schematically illustrates second means for synchronizing the video signals issuing from the eye and scene observing cameras of a device according to the invention.

Said casing of said removable module may advantageously contain means for pre-processing the video signals delivered by said video cameras 3, 5, particularly those described in FIGS. 2 and 4.

Figure 1:
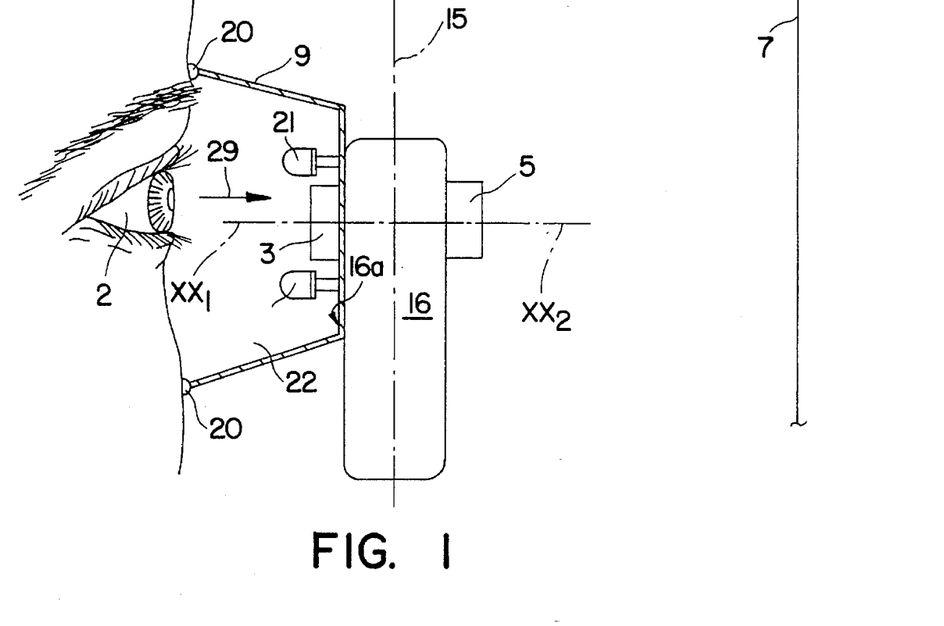
FIG. 1 schematically illustrates, in transverse view, a device according to the invention placed on the head of a patient observing a scene.

Said module or casing 16 may be easily mounted and dismantled manually on a mask 9 worn by the patient and having the general form of a spectacle frame.

Said module 16 may be mounted tightly so as to obturate by its face 16a an opening provided in the front part of said mask or said spectacle frame; said mask may for example comprise two openings respectively located opposite the patient's eyes, of which one may be equipped with one of said modules and the second opening may for example be equipped with a card likewise obturating in manner tight to the outside visible light, the inner volume 22 located near the patient's eyes and delimited by said mask, so as to constitute in front of the patient's eyes a black chamber, i.e. a chamber isolated from the visible light outside said mask, in order, for example, to make vestibular tests.

To that end, said mask may be provided on its face coming into contact with the patient's head, with sealing means 20 ensuring darkness in said chamber 22.

Said module 16 is provided to that end, on its inner face, with electroluminescent diodes 21 emitting light in the infrared or near infrared domain, in order to light the eyes of the patient in the dark and to allow said video camera 3 which is sensitive to infrared or near infrared radiation, to observe the movements of the eye 2 of the patient in the darkness of said chamber 22.

According to the invention, said cameras 3 and 5 with respective optical axes XX1 and XX2 which are substantially merged and substantially parallel and close to the direction 29 of the patient's look, are mounted "head-to-tail" inside and/or on said module 16.

Figure 3:
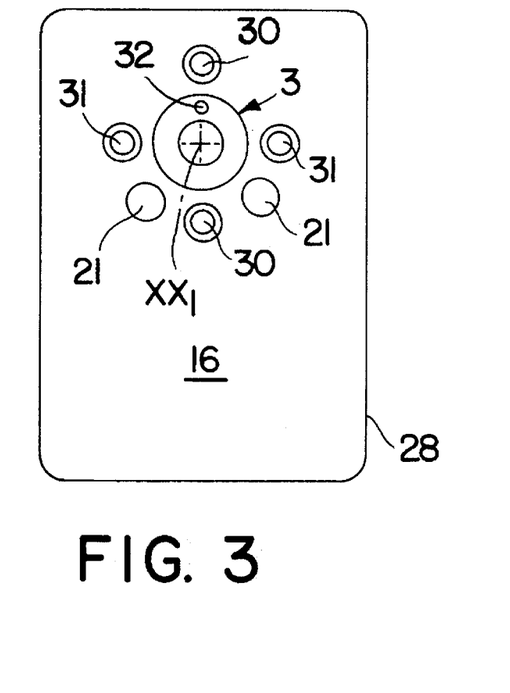
FIG. 3 illustrates the face of a removable module of a device according to the invention, which is located towards the patient's eye, and which corresponds to a particular embodiment comprising luminous photodiodes or photoreceptors whose pass band may be higher than 250 Hertz.

Referring to FIG. 3 in the case of it being desired to observe the movements of the patient's eyes with a pass band higher than 25 Hertz which is the usual pass band of the standard video signals delivered by the CCD sensors of cameras conventionally used, it is possible to equip the inner face of said module 16 with photodiodes 30, 31 or photoreceptors sensitive to the infrared light emitted by said electroluminescent diodes 21; to that end, it is advantageous to provide at least three photoreceptors 30, 31, for example four, as illustrated in FIG. 3; in this embodiment, two photoreceptors 30 mounted on either side of said camera, superposed substantially vertically, make it possible to detect the vertical movements of the eye observed, by digitalizing the voltage delivered by a high frequency analysis stage of which the differential inputs receive the signals of said photodiodes or photoreceptors.

In the same way, two photodiodes or photoreceptors 31 located on either side of said camera 3 and located substantially on the same horizontal axis make it possible to deliver a voltage from the differential analysis stage of the signals issuing from these photoreceptors.

The inner face of the casing 28 of the module 16 illustrated in FIG. 3 may also be provided with an electroluminescent diode 32, emitting visible light and also located near the lens of the camera 3 with optical axis XX1.

With reference to FIG. 2, the device may be used for multiplexing the signal 4 delivered by said eye observing camera (reference 3 in FIG. 1) and the video signal 6 delivered by said scene observing camera (reference 5 in FIG. 1).

A first multiplexed video signal 12 may be obtained which is constituted for example by the even frame of the first video signal 4 and by the odd frame of the second video signal 6; to that end, said video signals 4 and 6 are alternately switched by two switches 26 and 27 which are controlled in phase opposition.

To that end, the video signal 6 is presented to a synchro-frame separator 23 which delivers a synchronization signal to a clock or monostable 24 whose output signal serves to control a switch 26; said output signal from said monostable also pilots via an inverter 25 said second switch 27, so that a first multiplexed video signal 12 is obtained at the output.

With reference to FIG. 4, a second system for multiplexing said video signals 4 and 6 may be used in order to facilitate and accelerate analysis of said video signals for the purposes of observation of the movement of the eye and the relative movements of the patient's head with respect to the scene and/or the patient's chest with respect to the scene.

To that end, said signals 4 and 6 are applied to the input of a mixer 33 or multiplexer, which reconstitutes a second multiplexed video signal 13 which comprises in each of its even or odd frames, lines issuing from the respectively even or odd frames of each of said signals 4 and 6, said multiplexer 33 being synchronized on one of said signals, for example signal 6, by a synchronization device 23.

Figure 5:
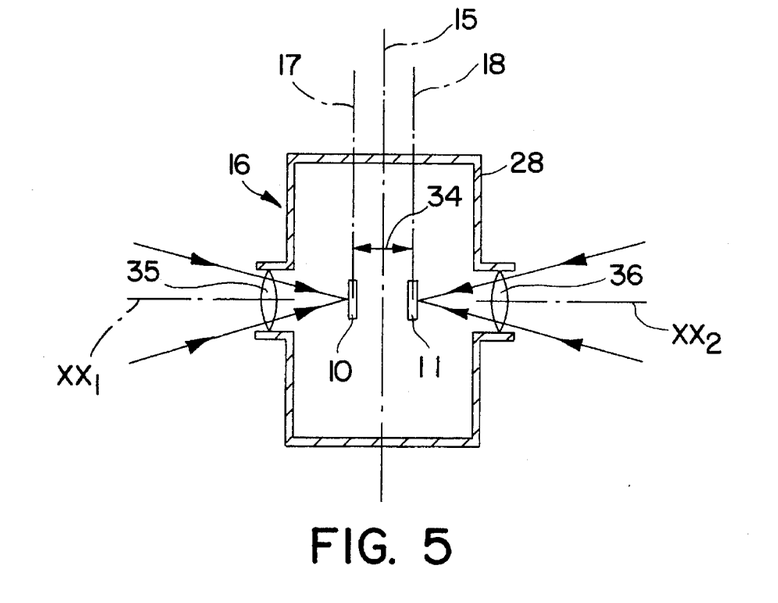
FIG. 5 schematically illustrates a view in transverse section in a substantially vertical plane, of a removable module of a device according to the invention.

With reference to FIG. 5, said eye observing video camera (reference 3 in FIG. 1), essentially comprises a monochrome matrix CCD sensor 10 which receives the light rays via optics or a lens 35, with optical axis XX1.

Said scene observing camera likewise integrated with the casing 28 of the module 16 which may be removably mounted on said mask, comprises a matrix CCD sensor 11 advantageously identical to said CCD sensor 10, and comprises optics 36 which may also be identical to optics 35 of said eye observing camera except for the adjustment of each focal distance to obtain the desired image sharpnesses.

Optics 36 may advantageously be equipped with a lens of very wide angle included between 90° and 180° to allow the objects of the scene always to be localized in the image, despite for example a very considerable rotation of the patient's head.

Said matrix CCD sensors 11 and 10 are advantageously respectively located in planes 18, 17 parallel to said plane of symmetry 15 and located at an equal distance therefrom so that the distance 34 between said CCD sensors 10 and 11 is small.

Figure 6:
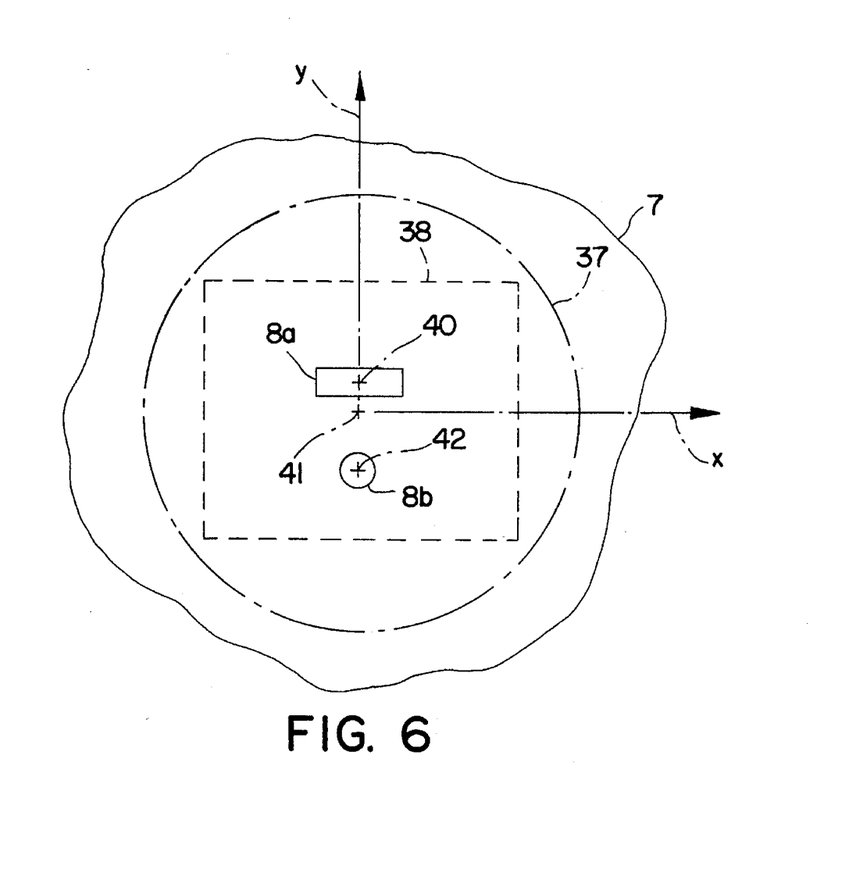
FIG. 6 schematically illustrates a scene and the marks with which it is provided.

FIG. 6 schematically illustrates a scene 7 with which may be associated a fixed mark 8a of substantially rectangular form and with centre 40.

FIG. 6 schematically shows the limit 37 of the field of vision observed by the scene camera of the device according to the invention, inside which may be predefined a window 38 for observation of the scene, which window is provided with a centre 41.

This Figure also illustrates a mark 8b for example of circular form and with centre 42, which mark 8b may be mobile and constituted by a light spot projected on said scene by a lighting device connected to the patient's chest and/or his head and/or to said removable module.

Figure 7:
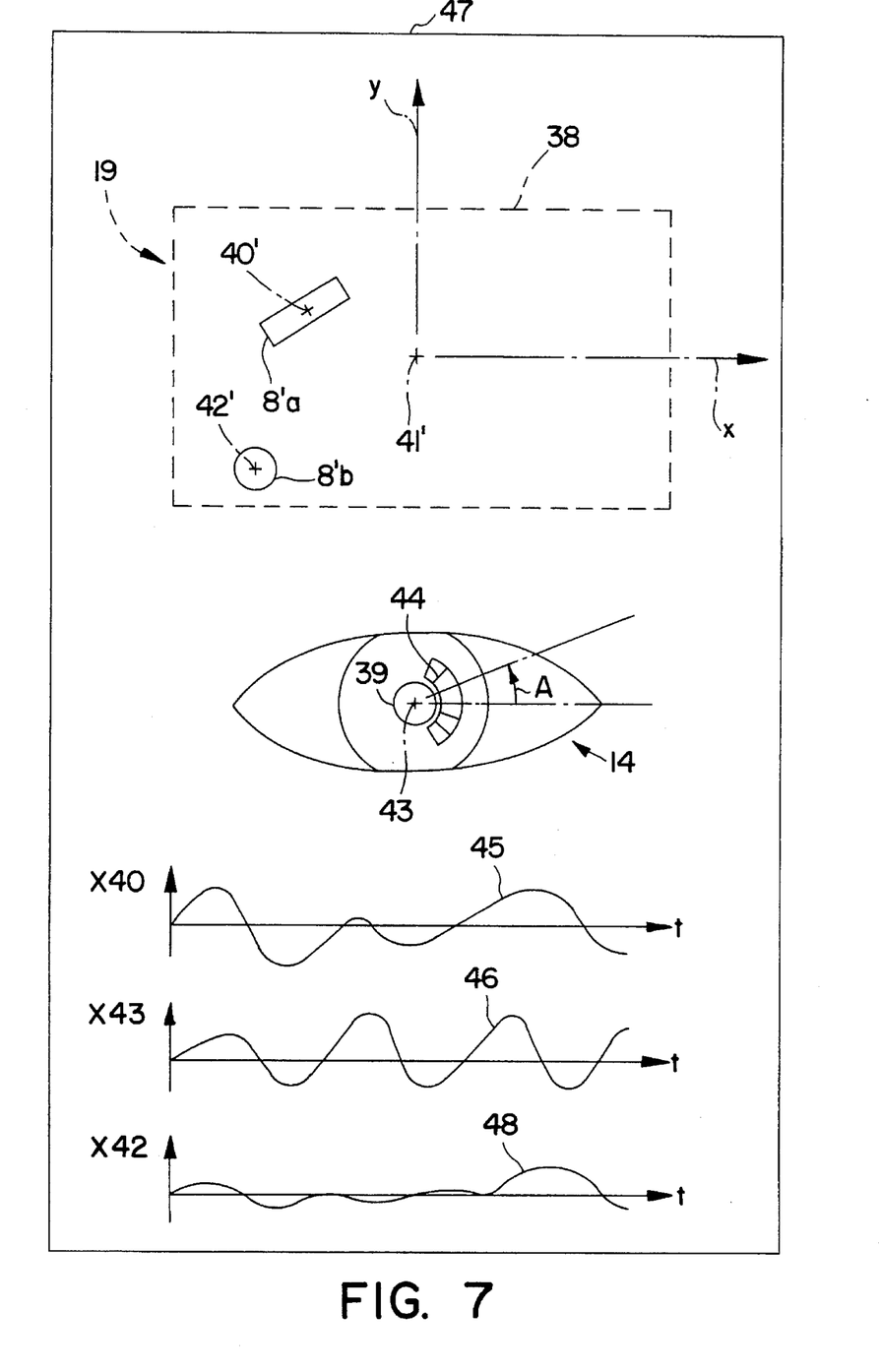
FIG. 7 illustrates a mode of displaying the results of measurement of the movements of the eye, using a device according to the invention.

FIG. 7 illustrates an example of display of the results of measurement of the movement of the eye and of the movement of the head with respect to the scene (with reference to an initial situation corresponding to FIG. 6), using a device according to the invention.

The results may be displayed on a screen 47 forming part for example of a micro-computer provided with conventional calculating and processing means.

There may be displayed on said screen 47, preferably simultaneously, for example at a frequency of the order of 25 Hertz, an image 19 corresponding to the scene observed by said scene camera, an image 14 corresponding to the image of the eye delivered by said camera of said eye observing module, as well as a timing diagram of the positions calculated at each instant of the centre of gravity of the different marks and of the pupil of the eye.

The upper part of FIG. 7 shows that said image 19 of the scene may be limited by said predetermined window 38 with centre 41'; in the plane of the Figure are marked X and Y axes passing through said centre 41 of said window.

Said mark 8a of FIG. 6 may, due to the movement of the patient's head, be notably transformed into a mark 8'a of similar shape and with centre 40', of which the position with respect to the centre 41' of said window has moved due to said movement of the head.

In the same way, on this image of the scene, a mark 8'b may be recognized, corresponding to said mark 8b of FIG. 6 and of which the position of the centre 42' with respect to the position of said centre 41' of said window 38 has also moved due for example to a movement of the patient's chest.

In the median part of FIG. 7 is also illustrated the image 14 of the eye obtained by said eye observing camera on which may be recognized the image 39 of the pupil of the eye, with centre or centre of gravity 43, of which the position in the plane of the Figure may be detected and measured in order to analyze the movements of the eye in response to stimuli.

The variation of the angular position A of the eye may for example be determined by measuring the angular position of a stria 44 which may be observed in a ring located around said pupil.

Advantageously, in a process according to the invention, the curves or timing diagrams 45, 46, 48 may be simultaneously displayed, corresponding to the evolution as a function of time t, respectively of the abscissa X40 of said fixed mark 8'*a* with respect to the centre of said observation window 38, of the abscissa X43 corresponding to the horizontal position of the centre of said pupil of said eye, and of the abscissa X42 corresponding to the horizontal position of said mobile mark 8'*b* associated with the position of the patient's torso.

The invention may be carried out by using for example a micro-computer equipped with a video signal acquisition card.

Advantageously, such a card may comprise a programmable video signal output on which may be connected a video projector; images comprising marks (targets or patterns) which will be projected by the video projector onto the screen which the patient is observing, may thus be synthesized.

According to this particular embodiment of the invention, one sole electronic card may be used for ensuring acquisition and digitalization of the signals delivered by said first and second cameras and for ensuring synthesis of one or more target images or marks, which presents a considerable advantage in economy and simplicity with respect to known devices making it possible to deliver targets in the patient's visual field, and which are generally constituted either by oculomotricity stimulators with electroluminescent diode bar or comprising a laser beam emitter, or by optokinetic reflex tracking stimulators with rotating projector of planetarium, Zeitoun mirror mosaic sphere type, these known devices being both very expensive and cumbersome. Furthermore, in this embodiment, the possibility of creating patterns is illimited; moreover, thanks to the fact that the same apparatus (the micro-computer suitably programmed) controls both the acquisition and digitalization of the images issuing from the video signals delivered by the cameras and the synthesis of the targets projected in the field of vision of the patient, the calculation of the movement of the eyes and/or of the head is facilitated thanks to the fact that the same software synthesizes said scene marks and this same software seeks the shape and calculates the position of these synthesized marks to calculate the movement of the patient's head deduced from the signals delivered by the cameras; it is thus advantageous, when the head movements are inscribed in a reduced angular range (more or less 60°), to synthesize by programmation the marks which are used for detecting the movement rather than to have to place contrasted and luminous or highly reflecting fixed marks in the scene, as this facilitates installation and use of the system for analyzing the movement of the eye.

According to a particular characteristic of the invention, the device may comprise a portable emitter of radioelectric signals which will be obtained or elaborated from said first and second video signals delivered by said first and second cameras, which emitter is carried by the patient, for example fixed on said frame.

This may make it possible to send the image of the patient's eye directly to a radioelectric signal receiver connected to the micro-computer or to the data-processing system, without using a connecting cable, which improves comfort of use; this process of use is particularly advantageous in the case of said first and second video signals being multiplexed to constitute one single multiplexed video signal, which, with the aid of one radio emitter assembly (carried by the patient) and radio receiver (connected to the computer or processor), facilitates receiving the images of the eye and of the scene on one sole acquisition and digitalization card integrated in the computer.

I claim:

1. A device for analyzing the movement of at least one eye of a patient when said patient is looking along a line of sight, said line of sight defined as a substantially horizontal plain extending from a pupil of said eye, said device comprising:

a frame which said patient wears on his face like a pair of eye spectacles, said frame encircling each of the eyes of said patient, said frame including openings therein for allowing said patient to see out of said frame;

a principal module removably attached to said frame such that one eye of said patient is associated with said principal module and wherein said principal module obturates said opening of said frame when attached thereto, said principle module comprised of a first CCD camera for observing movements of said one eye and capable of delivering a first video signal representative of an image of said one eye, and a second CCD camera for observing movements of a predetermined scene which said eye is required to view, said second camera capable of delivering a second video signal representative of an image of said scene, which said scene is located in the vicinity of said patient, said principal module including at least one light-emitting diode for illuminating said eye with infrared light;

at least one horizontally operating photoreceptor for receiving infrared light reflected from said one eye, said horizontal receptor determining horizontal movements of said same one eye;

at least one vertically operating photoreceptor for receiving infrared light reflected from said one eye, said vertical receptor determining vertical movements of said same one eye;

a second means for digitizing said second video signal and analyzing and processing said second digital signal by identifying at least one image appearing in said scene through contour extraction means, and then calculating a series of coordinates of said object of said scene;

a first means for digitizing said first video signal and analyzing and processing said first digital signal by identifying said pupil of said eye through contour extraction means and then calculating a series of coordinates of a center of said pupil;

a first means for synchronizing said first and second video signals and a first means for multiplexing said first and second video signals in order to form a first multiplexed video signal comprised of two odd and even frames, one of said one and even frames being identical to a simultaneous frame of said first video signal and the other of said odd and even frames identical to a simultaneous frame of said second video signal;

a second means for synchronizing said first and second video signals and a second means for multiplexing said first and second video signals in order to form a second multiplexed video signal, said second multiplexed signal comprised of two odd and even frames, each of said frames comprising a consecutive assembly of alternating lines, said assembly of alternating lines identical to a set of lines associated with said first and second video cameras;

wherein said first video camera has a first optical axis and said second video camera has a second optical axis, each of said cameras connected together such that each of said respective optical axes exist on a common optical camera plane, said optical camera plane generally coexisting with said line of sight, said first optical axis extending towards the pupil and said second optical axis extending in a substantially opposed direction, said common optical camera plane allowing said device to directly correlate observed eye movements of said first video camera with said scenic movements observed by said other eye and recorded by said second video camera.

2. The device of claim 1, wherein said frame is provided with a light-blocking means on said frame for forming an outside, visible light-blocking chamber over at least one of said eyes of said patient.

3. The device of claim 1, wherein said scene comprises one of a fixed or mobile contrasted mark, and said device includes a means for projecting at least one light spot constituting said mark.

4. The device of claim 1, further including a portable emitter for relaying of radioelectric signals obtained from said first and second video signals.

5. The device of claim 1, further including a second module removably attached to said frame such that said other eye of said patient is associated with said second module and wherein said second module obturates said other opening on said frame which is associated with said other eye, said second module comprised of a third CCD camera and a second light-emitting diode which illuminates said other eye with infrared light.

6. The device of claim 1, wherein said frame includes at least two openings therein, each of said modules blocking said openings when attached to said frame, said openings providing an angle of view 25° above and below said line of sight when said modules are removed from said frame.

7. Device for analyzing the movement of the eye of a patient comprising:

a spectacle frame provided with an opening in front part of said spectacle frame;

a first video camera adapted to deliver a first video signal representative of an image of said eye;

a second video camera adapted to deliver a second video signal representative of an image of a scene in which said patient is placed;

a casing removably mounted on said spectacle frame so as to obturate said opening;

said casing receiving said first and second video cameras;

said first and second video camera being mechanically rigidly connected together and being positioned with respect to each other so that respective image focal planes of said first and second video cameras are close.

8. Device for analyzing the movement of the eye of a patient comprising;

a mask provided with first and second opening in front part of said mask;

a first video camera adapted to deliver a first video signal representative of an image of said eye;

a second video camera adapted to deliver a second video signal representative of an image of a scene in which said patient is placed;

a first module removably mounted on said mask so as to obturate said first opening;

said first module receiving said first and second video cameras;

said first and second video camera being mechanically rigidly connected together;

said first and second video camera being mounted in a head to tail configuration and being positioned with respect to each other so that respective optical focus of said first and second video cameras are close and so that their respective optical axes are merged;

a second module removably mounted on said mask so as to obturate said second opening, at least one of said first and second modules comprising means for lighting said eye with infrared light.

* * * * *